United States Patent
Haider

(10) Patent No.: US 11,129,596 B2
(45) Date of Patent: Sep. 28, 2021

(54) SYSTEMS AND METHODS FOR ULTRASOUND MULTIPLEXING

(71) Applicant: General Electric Company, Schenectady, NY (US)

(72) Inventor: Bruno Hans Haider, Rehoboth Beach, DE (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1226 days.

(21) Appl. No.: 15/287,318

(22) Filed: Oct. 6, 2016

(65) Prior Publication Data
US 2018/0098753 A1   Apr. 12, 2018

(51) Int. Cl.
*A61B 8/00* (2006.01)
*H04B 3/32* (2006.01)
(Continued)

(52) U.S. Cl.
CPC .............. *A61B 8/5207* (2013.01); *A61B 8/54* (2013.01); *G01S 7/023* (2013.01); *G01S 7/5205* (2013.01); *G01S 7/52034* (2013.01); *G01S 7/52082* (2013.01); *G01S 15/8915* (2013.01); *H04B 3/32* (2013.01); *A61B 8/4444* (2013.01); *A61B 8/4483* (2013.01); *A61B 8/5269* (2013.01)

(58) Field of Classification Search
CPC ......... A61B 8/5207; A61B 8/54; A61B 8/145; A61B 8/5269; A61B 8/4483; A61B 8/4444; A61B 8/467; A61B 8/4427; A61B 8/461; A61B 2562/12; A61B 8/58; A61B 8/44; G01S 15/8915; G01S 7/5205; G01S 7/52034; G01S 7/52082; G01S 7/023; H04B 3/32; B06B 1/0292

See application file for complete search history.

(56) References Cited

U.S. PATENT DOCUMENTS 4,516,126 A * 5/1985 Masak ................. H01Q 3/2617
                                                      342/383
4,803,727 A * 2/1989 Holt ...................... H04B 14/046
                                                      381/1

(Continued)

OTHER PUBLICATIONS

Haider, Bruno Hans et al., "Ultrasound Transducer with Variable Pitch," U.S. Appl. No. 15/287,206, filed Oct. 6, 2016, 29 pages.

*Primary Examiner* — Michael J Tsai
*Assistant Examiner* — Johnathan Maynard
(74) *Attorney, Agent, or Firm* — McCoy Russell LLP

(57) ABSTRACT

Methods and systems are provided for ultrasound multiplexing. In one embodiment, a system comprises: an ultrasound probe comprising a transducer array and a multiplexer, wherein for a first signal and a second signal originating at the transducer array, the multiplexer multiplexes a sum signal and a difference signal formed from the first and the second signals into a multiplexed signal; and a console coupled to the ultrasound probe via a cable, the console including a processor, wherein the console receives the multiplexed signal via the cable, and wherein the processor generates an image from the first signal and the second signal recovered from the multiplexed signal. In this way, the number of processing channels can be reduced, thereby enabling a smaller ultrasound device with less hardware, while also avoiding signal degradation from channel crosstalk and transmission variation.

19 Claims, 4 Drawing Sheets

(51) Int. Cl.
    *A61B 8/08*     (2006.01)
    *G01S 7/02*     (2006.01)
    *G01S 7/52*     (2006.01)
    *G01S 15/89*     (2006.01)

(56) References Cited

U.S. PATENT DOCUMENTS

| | | | |
|---|---|---|---|
| 5,402,369 A * | 3/1995 | Main | G06F 7/5334 |
| | | | 708/620 |
| 5,622,177 A | 4/1997 | Breimesser et al. | |
| 6,168,564 B1 | 1/2001 | Teo | |
| 6,484,191 B1 * | 11/2002 | Alexandru | G06T 7/00 |
| | | | 702/179 |
| 6,506,160 B1 * | 1/2003 | Van Stralen | G01S 15/8952 |
| | | | 600/459 |
| 6,967,975 B2 | 11/2005 | Van Stalen et al. | |
| 8,226,563 B2 | 7/2012 | Peteresen et al. | |
| 8,551,004 B2 | 10/2013 | Adams et al. | |
| 2004/0002652 A1 * | 1/2004 | Phelps | G01S 7/5202 |
| | | | 600/437 |
| 2008/0130415 A1 | 6/2008 | Tai | |
| 2008/0133625 A1 * | 6/2008 | Alexandru | H03H 17/023 |
| | | | 708/101 |
| 2013/0023225 A1 * | 1/2013 | Weber | G01S 7/023 |
| | | | 455/296 |
| 2013/0029585 A1 * | 1/2013 | Kroeger | H04B 1/1036 |
| | | | 455/3.01 |
| 2013/0310983 A1 * | 11/2013 | Shimizu | H02N 2/16 |
| | | | 700/275 |

* cited by examiner

SYSTEMS AND METHODS FOR ULTRASOUND MULTIPLEXING

FIELD

Embodiments of the subject matter disclosed herein relate to ultrasound imaging, and more particularly, to multiplexing for ultrasound imaging systems.

BACKGROUND

Medical diagnostic ultrasound is an imaging modality that employs ultrasound waves to probe the acoustic properties of the body of a patient and produce a corresponding image. Generating of sound wave pulses and detection of returning echoes is typically accomplished by an ultrasound probe having one or more transducers. Such transducers typically include electromechanical elements capable of converting electrical energy into mechanical energy for transmission of ultrasonic waves into patient tissue and mechanical energy back into electrical energy when the reflected ultrasonic waves reach the transducers.

Typically, a separate coaxial cable for each transducer element is used to transmit ultrasound data from the ultrasound probe to an ultrasound processing console. For ultrasound devices with hundreds of transducer elements, the number of coaxial cables becomes cumbersome. It is therefore desirable to reduce the size or the number of cables so that an ultrasound device is easier to manipulate.

One approach to reducing the size of the cables is to utilize fiber optic cable instead of coaxial cable. However, the use of fiber optic cable requires that the analog ultrasound signals are converted to digital signals prior to transmission through the fiber optic cables. While the size of the cable bundle may be reduced as a result, the ultrasound probe necessarily becomes larger with the inclusion of hundreds of analog-to-digital converters.

Another approach to reducing the size or number of cables is to multiplex the ultrasound signals. However, the ultrasound signals can potentially become degraded when directly multiplexed and transmitted. It is therefore desirable to reduce the size and hardware complexity of an ultrasound system without potentially degrading the ultrasound signals.

BRIEF DESCRIPTION

In one embodiment, a system comprises: an ultrasound probe comprising a transducer array and a multiplexer, wherein for a first signal and a second signal originating at the transducer array, the multiplexer multiplexes a sum signal and a difference signal formed from the first and the second signals into a multiplexed signal; and a console coupled to the ultrasound probe via a cable, the console including a processor, wherein the console receives the multiplexed signal via the cable, and wherein the processor is configured with instructions in non-transitory memory that when executed cause the processor to generate an image from the first signal and the second signal recovered from the multiplexed signal. In this way, the number of processing channels can be reduced, thereby enabling a smaller ultrasound device with less hardware, while also avoiding signal degradation from channel crosstalk and transmission variation.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 2:
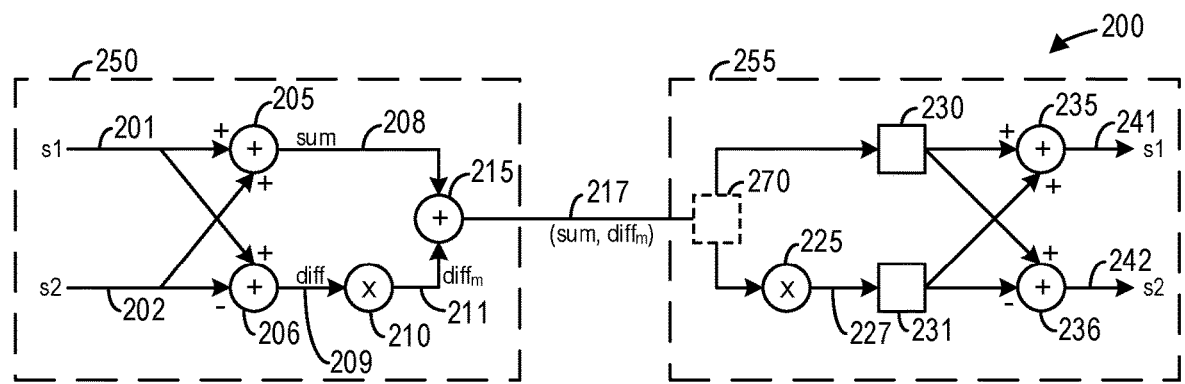
FIG. 2 shows a schematic block diagram illustrating an example multiplexing system for multiplexing two signals in an ultrasound system according to an embodiment of the invention.
Figure 3:
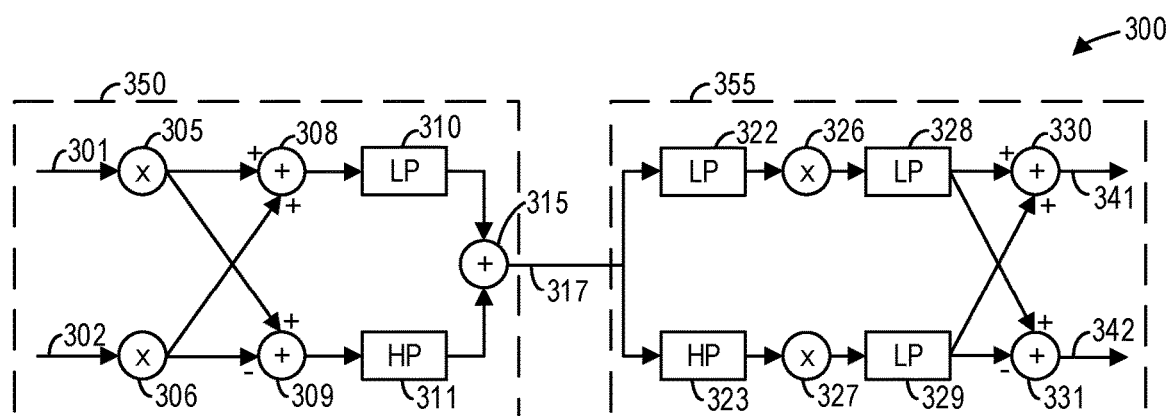
FIG. 3 shows a schematic block diagram illustrating another example multiplexing system for multiplexing two signals in an ultrasound system according to an embodiment of the invention.
Figure 4:
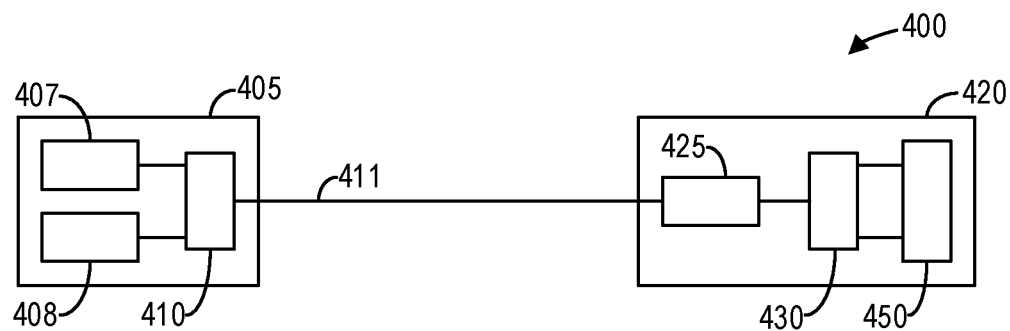
FIG. 4 shows a block diagram illustrating an example multiplexing configuration according to an embodiment of the invention.
Figure 5:
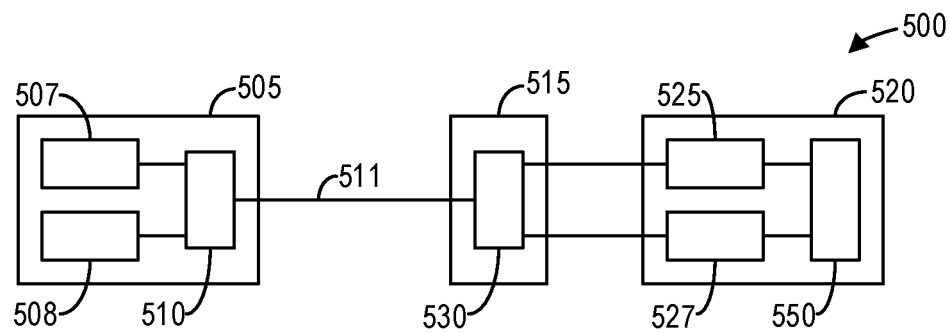
FIG. 5 shows a block diagram illustrating another example multiplexing configuration according to an embodiment of the invention.
Figure 6:
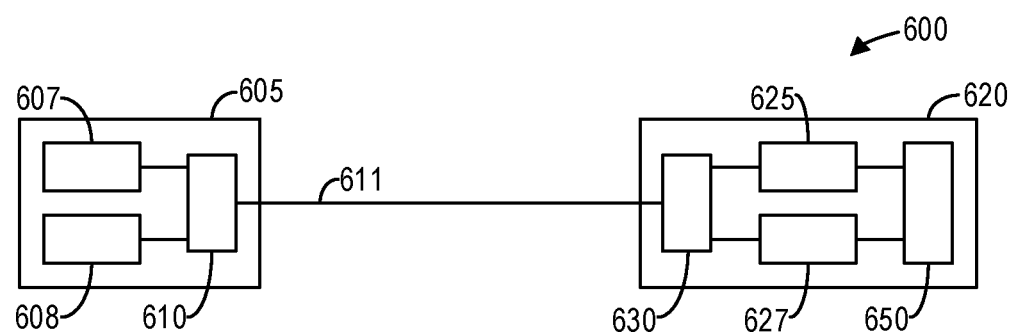
FIG. 6 shows a block diagram illustrating yet another example multiplexing configuration according to an embodiment of the invention.

The following description relates to various embodiments of an ultrasound imaging system. In particular, systems and methods are provided for multiplexing ultrasound signals. An indirect multiplexing method may be implemented in an ultrasound imaging system such as the system shown in FIG. 1. An indirect multiplexing method may multiplex combinations of ultrasound signals rather than the signals themselves, as shown in FIGS. 2 and 3. Various multiplexer configurations are shown in FIGS. 4-6. A method for calibrating a multiplexing system, such as the method shown in FIG. 7, includes characterizing transmission channels of a cable so that the degradation of signals transmitted through the transmission channels can be corrected.

Figure 1:
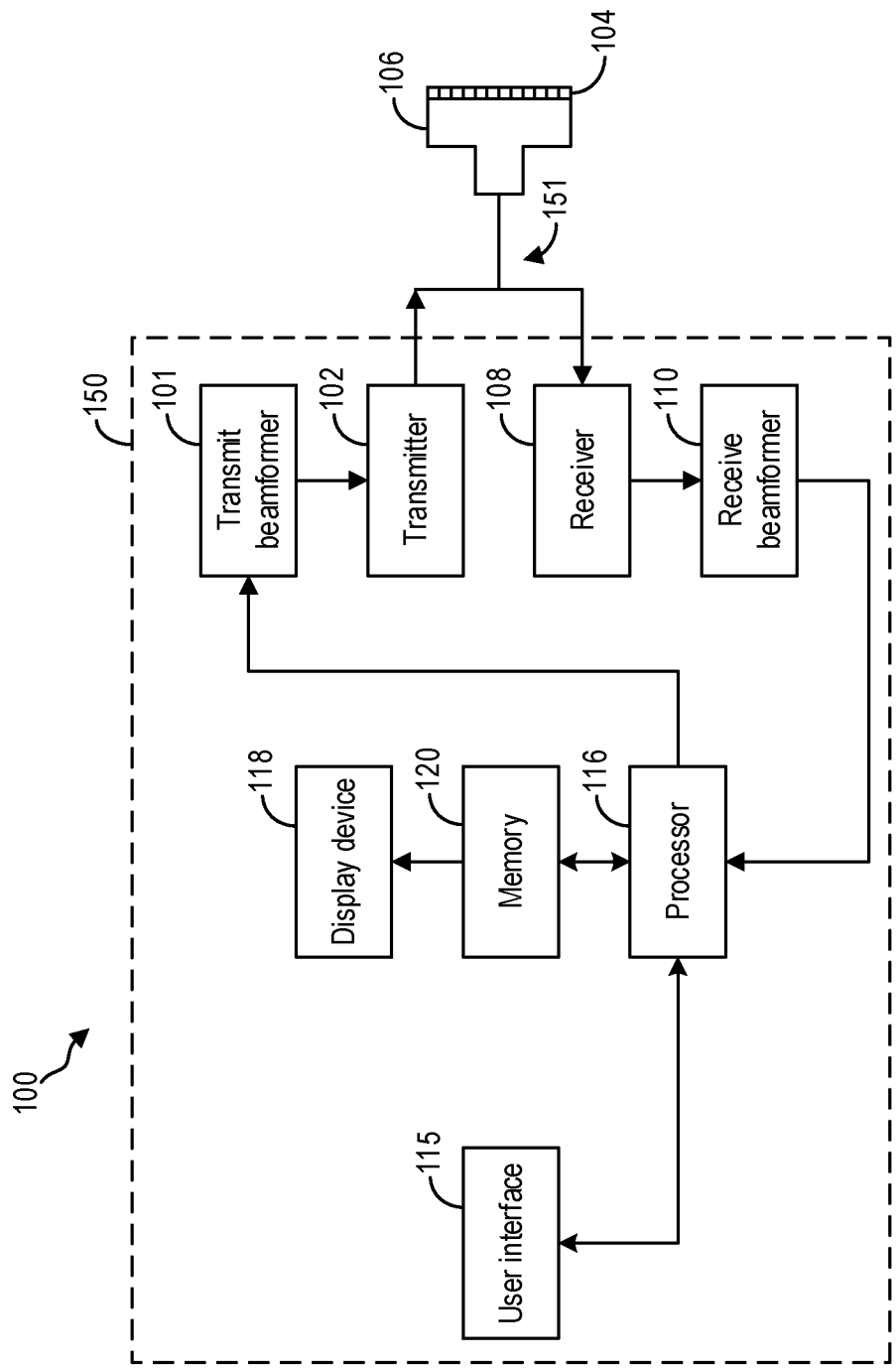
FIG. 1 shows an ultrasonic imaging system according to an embodiment of the invention.

FIG. 1 is a schematic diagram of an ultrasound imaging system 100 in accordance with an embodiment of the invention. The ultrasound imaging system 100 includes a transmit beamformer 101 and a transmitter 102 that drive elements 104 within a transducer array, or probe, 106 to emit pulsed ultrasonic signals into a body (not shown). According to an embodiment, the transducer array 106 may be a one-dimensional transducer array probe. However, in some embodiments, the transducer array 106 may be a two-dimensional matrix transducer array probe. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106.

The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like. The user interface 115 may include one or more of the following: a rotary, a mouse, a keyboard, a trackball, hard keys linked to specific actions, soft keys that may be configured to control different functions, and a graphical user interface displayed on the display device 118.

The ultrasound imaging system 100 also includes a processor 116 to control the transmit beamformer 101, the transmitter 102, the receiver 108, and the receive beamformer 110. The processor 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds' worth of volumes of ultrasound data. The volumes of data are stored in a manner to facilitate retrieval thereof according to its order or time of acquisition. The memory 120 may comprise any known data storage medium.

Optionally, embodiments of the present invention may be implemented using contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

In some examples, an ultrasound console 150 may house the user interface 115, the processor 116, the memory 120, and the display device 118. The ultrasound console 150 may further house the transmit beamformer 101, the transmitter 102, the receiver 108, and the receive beamformer 110. The console 150 may thus be coupled to the probe 106 via a cable 151. As discussed further herein, received ultrasound data may be transmitted from the probe 106 to the console 150 via the cable 151 using an indirect multiplexing method. In this way, the number of cables or cable channels necessary for transmitting received ultrasound data to the console 150 may be reduced by as much as half.

FIG. 2 shows a schematic block diagram illustrating an example multiplexing system 200 for multiplexing two signals in an ultrasound system according to an embodiment of the invention. Multiplexing system 200 includes a multiplexer 250 and a de-multiplexer 255. Instead of multiplexing the two signals directly, the sum and the difference of the signals are multiplexed and transmitted over a cable, and the original two signals are recovered from the sum and the difference.

The two signals, first signal 201 (s1) and second signal 202 (s2), comprise received ultrasound signals and therefore originate at or are generated in an ultrasound probe, which may comprise the ultrasound probe 106. The signals 201 and 202 are input at the probe into a multiplexer 250. Therein, the signals 201 and 202 are input to the summing junction 205 and added together at 205 to create the sum signal 208 (sum=s1+s2). The signal 201 and the negative of the signal 202 are also input to the summing junction 206 and added together at 206 to create the difference signal 209 (diff=s1−s2).

The difference signal 209 is modulated by modulator 210 to create a modulated difference signal 211. In some examples, the difference signal 209 is modulated at 210 with a square wave. Modulation with a square wave is more power efficient and requires less electronic space than modulation with a sinusoidal wave. However, it should be appreciated that in some examples, the difference signal 209 may be modulated at 210 using a modulation scheme other than a square wave.

Summer 215 adds the sum signal 208 and the modulated difference signal 211 into a multiplexed signal 217. The summer or summing junction 215 may comprise a simple summing function which adds the signals 208 and 211 together. Summer 215 may be implemented as a specific circuit (e.g., a summing amplifier) or as a physical summer (e.g., simply connecting signals 208 and 211 together if those signals are currents).

The multiplexed signal 217 is then transmitted over a channel of the cable connecting the ultrasound probe to the ultrasound console, such as the cable 151 coupling the probe 106 to the console 150 in FIG. 1. It should be noted that the modulation of the difference signal 209, as well as the summing of the modulated difference signal 211 with the sum signal 208, increases the bandwidth of the signal being transmitted over the cable in comparison to the bandwidth of a non-multiplexed signal transmitted over the same cable.

At the de-multiplexer 255, the multiplexed signal 217 is input separately to the low-pass filter 230 and the modulator 225. The modulator 225 de-modulates the multiplexed signal 217, and the de-modulated multiplexed signal 227 is input to a low-pass filter 231 similar to the low-pass filter 230. The low-pass filters 230 and 231 eliminate higher-frequency components from the multiplexed signal 217 and the de-modulated multiplexed signal 227, respectively.

The filtered multiplexed signal and filtered de-modulated multiplexed signal are then input to both the summing junction 235 and the summing junction 236, wherein the negative of the filtered de-modulated multiplexed signal is input to the summing junction 236. At summing junction 235, the first signal 241 is recovered, while at summing junction 236, the second signal 242 is recovered.

In some examples, the second multiplexer or de-multiplexer 255 includes a filter 270 configured to correct for cross-talk effects and other effects resulting from multiplexing such as signal attenuation, phase distortion, and amplitude distortion. For example, due to transmission and multiplexing errors, one would expect that the recovered signals are not equivalent to the original signals. For example, assume that de-multiplexed signals A' and B' respectively include errors da and db, such that:

$$A'=A(1+da), B'=B(1+db),$$

where A and B are the original un-multiplexed sum and difference signals. Then the sum X and the difference Y of the de-multiplexed signals is:

$$X=A'+B'=A(1+da)+B(1+db),$$

$$Y=A'-B'=A(1+da)-B(1+db).$$

If the signal A corresponds to the sum signal 208 while the signal B corresponds to the difference signal 209 (ignoring the square wave modulation), such that A=s1+s2 while B=s1−s2, then the sum X is:

$$X = (s1 + s2)(1 + da) + (s1 - s2)(1 + db)$$
$$= s1(2 + da + db) + s2(da - db),$$

while the difference Y is:

$$Y = (s1 + s2)(1 + da) - (s1 - s2)(1 + db)$$
$$= s2(2 + da + db) + s1(da - db).$$

The desired term in X, the signal s1, has an error term (2+da+db), while the desired term in Y, the signal s2, has the same error term (2+da+db). The crosstalk term in X (i.e., the signal s2), and the crosstalk term in Y (i.e., the signal s1) have identical factors of (da−db). If da and db are real-valued numbers, then the errors correspond to gain errors; if da and db are complex-valued numbers, then the errors correspond to phase and gain errors.

Thus, the errors in each recovered signal are similar and there is no preferential degradation of one particular signal. Regardless, as discussed further herein, the filter 270 corrects crosstalk and attenuation errors that may correspond to the error terms described above. Although a single filter 270 is depicted as filtering the multiplexed signal 217, in some examples the filter 270 may be implemented as a pair of filters positioned after the low-pass filters 230 and 231. In other examples, the filter 270 may be implemented as two filters positioned after the summing junctions 235 and 236. In this way, the recovered signals 241 and 242 are substantially close to the original signals 201 and 202.

A processor of the ultrasound console, such as processor 116 of the console 150, may then receive the recovered signals 241 and 242, and generate an ultrasound image from the recovered signals 241 and 242.

It should be appreciated that, as depicted, certain steps of the multiplexing method are carried out in the multiplexer 250 which may be positioned at the ultrasound probe (such as the probe 106), while other steps of the multiplexing method are carried out in the second multiplexer or the de-multiplexer 255 which may be positioned at the ultrasound console (such as the console 150). For example, the ultrasound signals are generated, combined into sum and difference signals, and multiplexed in the multiplexer 250. Meanwhile, the de-multiplexing of the transmitted multiplexed signal and the recovering of the combining the sum and difference signals to recover the ultrasound signals occurs in the de-multiplexer 255. As discussed further herein, it should be appreciated that certain steps may be executed outside of the probe and the console. For example, the multiplexer 255 used for de-multiplexing may be positioned in a connector that connects the cable to the console, as described further herein with regard to FIG. 5.

Thus, a method for multiplexing ultrasound signals is provided, the method comprising: generating, with an ultrasound probe, a first ultrasound signal and a second ultrasound signal; combining the first and the second ultrasound signals into a sum signal and a difference signal; modulating the difference signal with a square wave; multiplexing the sum signal and the modulated difference signal into a multiplexed signal; transmitting the multiplexed signal over a cable coupling the ultrasound probe to an ultrasound console; de-multiplexing the multiplexed signal into the sum signal and the modulated difference signal; de-modulating the modulated difference signal to recover the difference signal; combining the sum signal and the difference signal to recover the first and the second ultrasound signals; and generating, with a processor, an image from the recovered first and second ultrasound signals.

FIG. 3 shows a schematic block diagram illustrating another example multiplexing system 300 for multiplexing two signals in an ultrasound system according to an embodiment of the invention. Multiplexing system 300 includes a multiplexer 350 and a de-multiplexer 355. Instead of multiplexing the two signals directly, the sum and the difference of the signals are multiplexed and transmitted over a cable, and the original two signals are recovered from the sum and the difference.

In contrast with the multiplexing system 200 described herein above, both the first signal 301 and the second signal 302 are respectively modulated via modulators 305 and 306 in the multiplexer 350. The modulated signals include both the upper and the lower sidebands. The modulated signals are then both input to summing junctions 308 to form a sum signal. The modulated signals are also both input to summing junction 309, wherein the negative of the modulated second signal is input to summing junction 309 as depicted to form the difference signal. The sum signal is input to a low-pass filter 310 while the difference signal is input to a high-pass filter 311. Thus the filtered sum signal retains the lower sideband while the filtered difference signal retains the upper sideband. The two branches are then added together at summing junction 315, and the resulting multiplexed signal 317 is transmitted over the cable coupling the probe to the console.

At the second multiplexer or de-multiplexer 355, the multiplexed signal 317 is input to both a low-pass filter 322 and a high-pass filter 323 which respectively separate out the lower and the upper sidebands from the multiplexed signal 317. The filtered signals are then de-modulated respectively by modulators 326 and 327. The de-modulated signals are then low-pass filtered by respective low-pass filters 328 and 329 to remove higher-frequency components from the demodulation process. The signals are then input to both summing junctions 330 and 331 to recover the first signal 341 and the second signal 342.

Although not depicted, it should be appreciated that the de-multiplexer 355 may include a filter similar to filter 270 depicted in FIG. 2 for correcting crosstalk and attenuation errors in the transmitted signals.

FIG. 4 shows a block diagram illustrating an example multiplexing configuration 400 according to an embodiment of the invention. In an ultrasound probe 405, channels 407 and 408 generate a first signal and a second signal, respectively.

The probe 405 includes a 2:1 frequency multiplexer 410 that multiplexes the first signal and the second signal. As non-limiting and illustrative examples, multiplexer 410 may comprise the multiplexer 250 described hereinabove with regard to FIG. 2 or the multiplexer 350 described hereinabove with regard to FIG. 3. The multiplexed signal output by the multiplexer 410 is transmitted over the cable 411 to the ultrasound console 420. At the ultrasound console 420, the multiplexed signal is converted from an analog signal to a digital signal by the analog-digital converter 425.

The digital multiplexed signal is then de-multiplexed by 2:1 frequency multiplexer 430 into the first signal and the second signal. As non-limiting and illustrative examples, the multiplexer 430 may comprise the de-multiplexer 255 described hereinabove with regard to FIG. 2 or the de-multiplexer 355 described hereinabove with regard to FIG. 3. The first signal and the second signal are then provided to the processor 450 positioned in the console. The processor 450 processes the first and second signals using software beamforming techniques. Thus, in some examples, the signals may be initially multiplexed in the analog domain, while the signals are de-multiplexed in the digital domain.

FIG. 5 shows a block diagram illustrating another example multiplexing configuration 500 according to an embodiment of the invention. In an ultrasound probe 505, channels 507 and 508 respectively generate a first signal and a second signal.

The probe 505 includes a 2:1 frequency multiplexer 510, which may comprise the multiplexer 250 or the multiplexer 350 described hereinabove, that multiplexes the first and second signals. The multiplexed signal is then transmitted from the ultrasound probe 505 over a cable 511 to the ultrasound console 520. The cable 511 may be connected to the ultrasound console 520 via a connector 515. The connector 515 includes a 2:1 frequency multiplexer 530, which may comprise the de-multiplexer 255 or the de-multiplexer 355 described hereinabove, that de-multiplexes the multiplexed signal back into the first and second signals.

The first and second signals are then converted from the analog domain to the digital domain via analog-digital converters 525 and 527, respectively. The first and second digital signals are then input to the processor 550 of the console 520 for software beamforming. Thus, in some examples, the multiplexing and de-multiplexing of the signals may occur entirely in the analog domain and outside of the ultrasound console.

FIG. 6 shows a block diagram illustrating yet another example multiplexing configuration 600 according to an embodiment of the invention. In an ultrasound probe 605, channels 607 and 608 respectively generate a first signal and a second signal.

The probe 605 includes a 2:1 frequency multiplexer 610, which may comprise the multiplexer 250 or the multiplexer 350 described hereinabove, that multiplexes the first and second signals. The resulting multiplexed signal is then transmitted over a cable 611 from the ultrasound probe 605 to an ultrasound console 620. The ultrasound console 620 includes a 2:1 frequency multiplexer 630, which may comprise one of the de-multiplexers 255 or 355 described hereinabove, that de-multiplexes the multiplexed signal into the first and second signals. The first and second signals are then converted from the analog domain to the digital domain via the analog-digital converters 625 and 627, respectively. The digital first and second signals are then input to the processor 650 of the ultrasound console for software beamforming.

Thus, in some examples, the signals may be multiplexed and de-multiplexed entirely in the analog domain, while the multiplexing occurs in the ultrasound probe and the de-multiplexing occurs in the ultrasound console.

Figure 7:
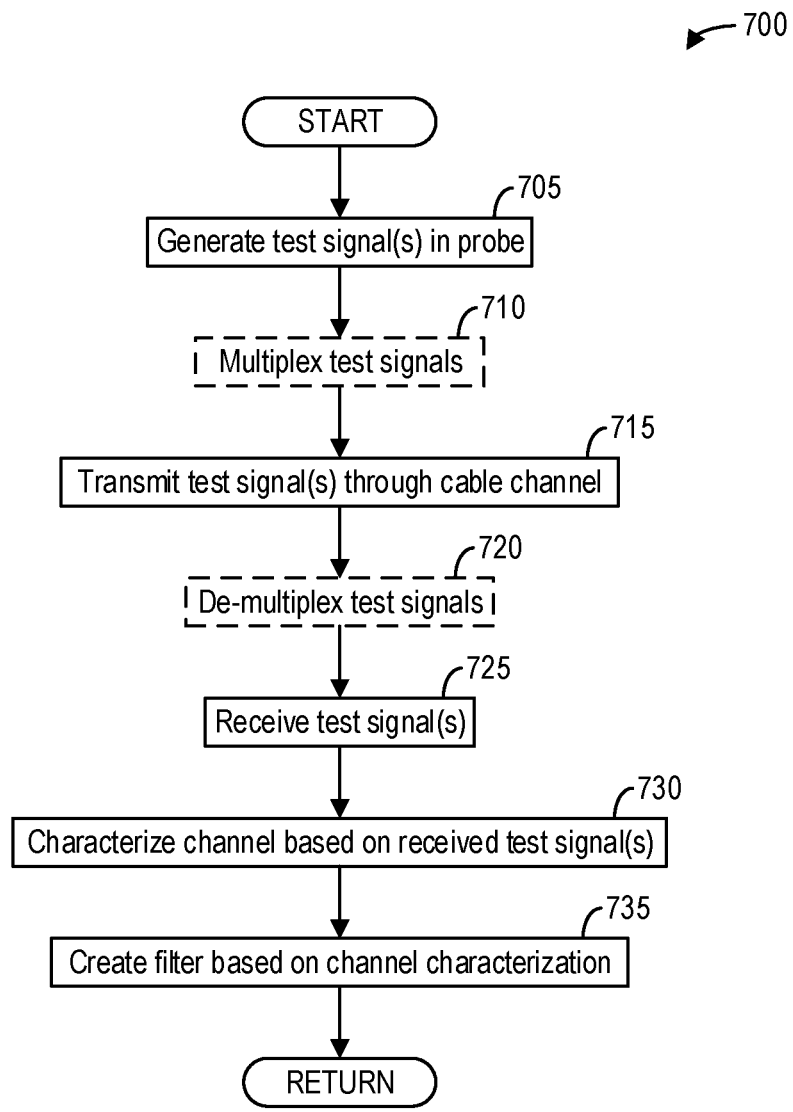
FIG. 7 shows a high-level flow chart illustrating an example method for calibrating an ultrasound multiplexing system according to an embodiment of the invention.

FIG. 7 shows a high-level flow chart illustrating an example method 700 for calibrating an ultrasound multiplexing system according to an embodiment of the invention. Method 700 will be described with reference to the systems and components of FIGS. 1-6, though it should be appreciated that the method may be applied to other systems and components without departing from the scope of the current disclosure. Method 700 may be implemented as executable instructions in non-transitory memory of processor 116.

Method 700 begins at 705. At 705, method 700 includes generating one or more test signals in the probe. If more than one test signal is generated in the probe, method 700 continues to 710. At 710, method 700 optionally includes multiplexing the test signals. The test signals may be multiplexed in accordance with the methods described herein above with regard to FIG. 2 or FIG. 3. For example, a first test signal and a second test signal may be combined into sum and difference signals, and square wave modulation may be applied to the difference signal. The method then multiplexes the sum signal and the modulated difference signal into a multiplexed test signal.

After multiplexing the test signals, or if only one test signal is generated at 705, method 700 proceeds to 715. At 715, method 700 includes transmitting the test signal(s) through the cable channel. If only one test signal is generated at 705, then the test signal is transmitted through the cable to the ultrasound console. If two test signals are generated at 705 and multiplexed at 710, the multiplexed signal is transmitted through the cable to the ultrasound console.

At 720, method 700 optionally includes de-multiplexing the test signals. Specifically, if a multiplexed test signal is transmitted at 715, then the method de-multiplexes, with a multiplexer such as the de-multiplexer 255 or the de-multiplexer 355, the multiplexed test signal into the test sum signal and the modulated difference signal. The modulated difference signal may be de-modulated to recover the difference signal. The sum signal and the difference signal may then be combined to recover the first test signal and the second test signal.

At 725, method 700 includes receiving the test signal(s). In examples wherein a single test signal is generated at 705, the processor may receive the single test signal. In examples wherein a first signal and a second signal are generated at 705, the processor receives the first and second test signals. Continuing at 730, method 700 includes characterizing the cable channel based on the received test signal(s). Specifically, the method compares the received test signal(s) to the test signal(s) originally generated at 705 to determine how the transmission of the test signal(s) affects the test signal.

Continuing at 735, method 700 includes creating a filter based on the channel characterization. The filter may be implemented, for example, as the filter 270 such that the filters correct for cross-talk and attenuation errors. In this way, signals may be multiplexed and transmitted from the probe to the console without degradation of the signals. Method 700 then ends.

A technical effect of the disclosure is the multiplexing of ultrasound signals. Another technical effect of the disclosure is the reduction of a number of cables or cable channels necessary for transmitting received ultrasound signals from an ultrasound probe to a processor. Yet another technical effect is the generation of an ultrasound image from ultrasound data transmitted through an indirect multiplexing system.

The systems and methods for ultrasound multiplexing provided herein allow for a reduced number of hardware channels for a larger number of ultrasound signals. A smaller cable provides improved ergonomics and lower manufacturing costs. Fewer console input channels allows for less hardware, less power consumption, and lower costs.

In one embodiment, a system comprises: an ultrasound probe comprising a transducer array and a multiplexer, wherein for a first signal and a second signal originating at the transducer array, the multiplexer multiplexes a sum signal and a difference signal formed from the first and the second signals into a multiplexed signal; and a console coupled to the ultrasound probe via a cable, the console including a processor, wherein the console receives the multiplexed signal via the cable, and wherein the processor is configured with instructions in non-transitory memory that when executed cause the processor to generate an image from the first signal and the second signal recovered from the multiplexed signal.

In a first example of the system, the difference signal is modulated with a square wave at the ultrasound probe prior to the multiplexing and de-modulated with the square wave at the console after de-multiplexing the multiplexed signal. In a second example of the system optionally including the first example, modulating the difference signal increases the bandwidth of the multiplexed signal relative to a multiplexed signal comprising the sum signal and the difference signal without modulation. In a third example of the system optionally including one or more of the first and second examples, the system further comprises a second multiplexer positioned at the console and configured to de-multiplex the multiplexed signal into the sum signal and the difference signal. In a fourth example of the system optionally including one or more of the first through third examples, the first signal and the second signal are recovered from the multiplexed signal by combining the sum signal and the difference signal obtained after de-multiplexing the multiplexed signal. In a fifth example of the system optionally including one or more of the first through fourth examples, the console includes at least one filter configured to correct cross-talk and attenuation errors in the sum signal and the difference signal obtained after de-multiplexing the signal. In a sixth example of the system optionally including one or more of the first through fifth examples, the console further includes at least one analog-to-digital converter configured to convert the de-multiplexed signals from an analog domain to a digital domain. In a seventh example of the system optionally including one or more of the first through sixth examples, the ultrasound probe includes at least two summing junctions configured to combine the first signal and the second signal into the sum signal and the difference signal, and wherein the console includes at least two summing junctions configured to combine the sum signal and the difference signal into the first signal and the second signal. In an eighth example of the system optionally including one or more of the first through seventh examples, the console further includes a display device coupled to the processor, and wherein the processor is further configured with instructions in the non-transitory memory that when executed cause the processor to display, via the display device, the generated image. In a ninth example of the system optionally including one or more of the first through eighth examples, the difference signal is modulated with a square wave at the ultrasound probe and de-modulated with the square wave at the console. In a tenth example of the system optionally including one or more of the first through ninth examples, the system further comprises a de-multiplexer positioned at the console and configured to de-multiplex the multiplexed signal into the sum signal and the difference signal. In an eleventh example of the system optionally including one or more of the first through tenth examples, the console includes at least one filter configured to correct cross-talk and attenuation errors in the multiplexed signal from the probe. In a twelfth example of the system optionally including one or more of the first through eleventh examples, the console further includes at least one analog-to-digital converter configured to convert the multiplexed signal from an analog domain to a digital domain.

In another embodiment, a system comprises: an ultrasound probe comprising an array transducer configured to generate a first signal and a second signal; a console coupled to the ultrasound probe via a cable, the console comprising a processor; a first multiplexer housed within the ultrasound probe and configured to multiplex the first signal and the second signal into a multiplexed signal; and a second multiplexer configured to de-multiplex the multiplexed signal into the first signal and the second signal after transmission of the multiplexed signal through the cable; wherein the processor is configured with instructions in non-transitory memory that when executed cause the processor to generate an image from the first signal and the second signal.

In a first example of the system, the second multiplexer is housed within a connector coupling the cable to the console. In a second example of the system optionally including the first example, the second multiplexer is housed within the console. In a third example of the system optionally including one or more of the first and second examples, the console includes an analog-to-digital converter that converts the multiplexed signal into a digital signal prior to the de-multiplexing. In a fourth example of the system optionally including one or more of the first through third examples, the console includes at least two analog-to-digital converters that convert the first signal and the second signal into digital signals after the de-multiplexing. In a fifth example of the system optionally including one or more of the first through fourth examples, the first multiplexer includes circuitry for combining the first and second signals into a sum signal and a difference signal, wherein the first multiplexer multiplexes the sum signal and the difference signal into the multiplexed signal, and wherein the second multiplexer includes circuitry for combining the sum signal and the difference signal to obtain the first and second signals.

In yet another embodiment, a method comprises: generating, with an ultrasound probe, a first ultrasound signal and a second ultrasound signal; combining the first and the second ultrasound signals into a sum signal and a difference signal; modulating the difference signal with a square wave; multiplexing the sum signal and the modulated difference signal into a multiplexed signal; transmitting the multiplexed signal over a cable coupling the ultrasound probe to an ultrasound console; de-multiplexing the multiplexed signal into the sum signal and the modulated difference signal; de-modulating the modulated difference signal to recover the difference signal; combining the sum signal and the difference signal to recover the first and the second ultrasound signals; and generating, with a processor, an image from the recovered first and second ultrasound signals.

In a first example of the method, the method further comprises filtering the sum signal and the difference signal based on a characterization of the cable prior to combining the sum signal and the difference signal to recover the first and the second ultrasound signals. In a second example of the method optionally including the first example, the characterization is obtained by: generating, with the ultrasound probe, a first test signal and a second test signal; combining the first test signal and the second test signal into a test sum signal and a test difference signal; modulating the test difference signal with the square wave; multiplexing the test sum signal and the modulated test difference signal into a multiplexed test signal; transmitting the multiplexed test signal over the cable; de-multiplexing the multiplexed test signal into a second test sum signal and a second modulated test difference signal; de-modulating the second modulated test difference signal to obtain a second test difference signal; combining the second test sum signal and the second test difference signal to obtain a third test signal and a fourth test signal; and characterizing properties of the cable based on a comparison of the third and fourth test signals with the first and second test signals to obtain the characterization. In a third example of the method optionally including one or more of the first and second examples, the characterization is obtained by: generating, with the ultrasound probe, a test signal; transmitting the test signal over the cable; receiving, with the processor, the test signal; and characterizing properties of the cable based on a comparison of the received test signal and the test signal to obtain the characterization. In a fourth example of the method optionally including one or more of the first through third examples, the method further comprises converting the multiplexed signal from an analog domain to a digital domain prior to the de-multiplexing.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A system, comprising:
an ultrasound probe comprising a transducer array and a multiplexer, wherein for a first signal and a second signal originating at the transducer array, the multiplexer multiplexes a sum signal and a difference signal formed from the first and second signals into a multiplexed signal;

a console coupled to the ultrasound probe via a cable, the console including a processor, wherein the console receives the multiplexed signal via the cable, the multiplexed signal sent via the cable being an analog signal, and wherein the processor is configured with instructions in non-transitory memory that, when executed, cause the processor to generate an image from the first signal and the second signal recovered from the multiplexed signal.

2. The system of claim 1, wherein the difference signal is modulated with a square wave at the ultrasound probe and de-modulated with the square wave at the console.

3. The system of claim 2, wherein modulating the difference signal increases a bandwidth of the multiplexed signal relative to a multiplexed signal comprising the sum signal and the difference signal without modulation.

4. The system of claim 1, further comprising a de-multiplexer positioned at the console and configured to de-multiplex the multiplexed signal into the sum signal and the difference signal.

5. The system of claim 4, wherein the first signal and the second signal are recovered from the multiplexed signal by combining the sum signal and the difference signal obtained after de-multiplexing the multiplexed signal.

6. The system of claim 4, wherein the console includes at least one filter configured to correct cross-talk and attenuation errors in the multiplexed signal from the ultrasound probe.

7. The system of claim 4, wherein the console further includes at least one analog-to-digital converter configured to convert the de-multiplexed signals from an analog domain to a digital domain.

8. The system of claim 1, wherein the console further includes at least one analog-to-digital converter configured to convert the multiplexed signal from an analog domain to a digital domain, wherein at the console, the multiplexed signal is converted from the analog signal to a digital signal by the analog-to-digital converter in the console before de-multiplexing the multiplexed signal.

9. The system of claim 1, wherein the ultrasound probe includes at least two summing junctions configured to combine the first signal and the second signal into the sum signal and the difference signal, and wherein the console includes at least two summing junctions configured to combine the sum signal and the difference signal into the first signal and the second signal.

10. The system of claim 1, wherein the console further includes a display device coupled to the processor, and wherein the processor is further configured with instructions in the non-transitory memory that, when executed, cause the processor to display, via the display device, the generated image.

11. A system, comprising:
an ultrasound probe comprising an array transducer configured to generate a first signal and a second signal;
a cable configured to transmit analog signals;
a console coupled to the ultrasound probe via a cable, the console comprising an analog-to-digital converter and a processor;
a first multiplexer housed within the ultrasound probe and configured to multiplex the first signal and the second signal into a multiplexed signal; and
a second multiplexer configured to de-multiplex the multiplexed signal into the first signal and the second signal after analog transmission of the multiplexed signal through the cable;
wherein the processor is configured with instructions in non-transitory memory that, when executed, cause the processor to generate an image from the first signal and the second signal.

12. The system of claim 11, wherein the second multiplexer is housed within a connector coupling the cable to the console.

13. The system of claim 11, wherein the second multiplexer is housed within the console, and wherein the analog-to-digital converter converts the analog signal transmitted over the cable before de-multiplexing, the analog-to-digital converter coupled to the cable before the second multiplexer.

14. The system of claim 11, wherein the console includes the analog-to-digital converter that converts the multiplexed signal into a digital signal prior to the de-multiplexing.

15. The system of claim 11, wherein the first multiplexer includes circuitry for combining the first and second signals into a sum signal and a difference signal, wherein the first multiplexer multiplexes the sum signal and the difference signal into the multiplexed signal, and wherein the second multiplexer includes circuitry for combining the sum signal and the difference signal to obtain the first and second signals.

16. A method, comprising:
generating, with an ultrasound probe, a first ultrasound signal and a second ultrasound signal;
combining the first and second ultrasound signals into a sum signal and a difference signal;
modulating the difference signal with a square wave;
multiplexing the sum signal and the modulated difference signal into a multiplexed signal;
transmitting the multiplexed signal over a cable coupling the ultrasound probe to an ultrasound console, the transmitted multiplexed signal being an analog signal;
converting the transmitted multiplexed signal from analog to digital at the console;
de-multiplexing the digitized multiplexed signal into the sum signal and the modulated difference signal;
de-modulating the modulated difference signal to recover the difference signal;
combining the sum signal and the difference signal to recover the first and second ultrasound signals; and
generating, with a processor, an image from the recovered first and second ultrasound signals.

17. The method of claim 16, further comprising filtering the sum signal and the difference signal based on a characterization of the cable prior to combining the sum signal and the difference signal to recover the first and second ultrasound signals.

18. The method of claim 17, wherein the characterization is obtained by:
generating, with the ultrasound probe, a first test signal and a second test signal;
combining the first test signal and the second test signal into a test sum signal and a test difference signal;
modulating the test difference signal with the square wave;
multiplexing the test sum signal and the modulated test difference signal into a multiplexed test signal;
transmitting the multiplexed test signal over the cable;
de-multiplexing the multiplexed test signal into a second test sum signal and a second modulated test difference signal;
de-modulating the second modulated test difference signal to obtain a second test difference signal;

combining the second test sum signal and the second test difference signal to obtain a third test signal and a fourth test signal; and characterizing properties of the cable based on a comparison of the third and fourth test signals with the first and second test signals to obtain the characterization.

19. The method of claim 17, wherein the characterization is obtained by:
generating, with the ultrasound probe, a test signal;
transmitting the test signal over the cable;
receiving, with the processor, the test signal; and
characterizing properties of the cable based on a comparison of the received test signal and the test signal to obtain the characterization.

* * * * *